(12) United States Patent
Davant, Jr. et al.

(10) Patent No.: US 6,440,172 B1
(45) Date of Patent: Aug. 27, 2002

(54) REINFORCED PROSTHETIC SLEEVE

(75) Inventors: J. Allison Davant, Jr.; David L. Glontz, both of Charlotte, NC (US)

(73) Assignee: Rx Textiles, Monroe, NC (US)

( * ) Notice: Subject to any disclaimer, the term of this patent is extended or adjusted under 35 U.S.C. 154(b) by 0 days.

(21) Appl. No.: 09/397,311

(22) Filed: Sep. 16, 1999

(51) Int. Cl.⁷ .................................................. A61F 2/80
(52) U.S. Cl. ........................................................ 623/36
(58) Field of Search .............................. 623/32, 33, 34, 623/35, 36, 37; 602/61–63; 128/892; 606/212; 2/16–24

(56) References Cited

U.S. PATENT DOCUMENTS

| | | | |
|---|---|---|---|
| 560,831 A | 5/1896 | Barroll | |
| 4,027,667 A | 6/1977 | Swallow et al. | |
| 4,180,869 A | 1/1980 | Pedergrass et al. | |
| 4,341,096 A | 7/1982 | Safrit et al. | |
| 4,424,596 A | 1/1984 | Jackson | |
| 4,571,960 A | 2/1986 | Hursh et al. | |
| 5,376,129 A | 12/1994 | Faulkner et al. | |
| 5,376,131 A | 12/1994 | Lenze et al. | |
| 5,571,208 A | * 11/1996 | Caspers | ........................ 623/32 |
| 5,673,433 A | * 10/1997 | Rothrum | ........................... 2/46 |
| 5,769,809 A | * 6/1998 | Witzel | .......................... 602/62 |
| 5,814,003 A | 9/1998 | Knox et al. | |
| 5,972,036 A | * 10/1999 | Kristinsson et al. | ........... 623/33 |
| 6,149,690 A | * 11/2000 | Belzidsky | ...................... 623/32 |

FOREIGN PATENT DOCUMENTS

LA 0086147 * 8/1983 .................. 623/36

* cited by examiner

*Primary Examiner*—David H. Willse
*Assistant Examiner*—Alvin Stewart
(74) *Attorney, Agent, or Firm*—Summa & Allan, P.A.

(57) ABSTRACT

A prosthetic sleeve for covering a gel sleeve having a reinforced circular opening at the distal end of the sleeve that is sewn or serged and then optionally coated with a gel to prevent unraveling of the yarn. The invention includes a knit sleeve having an upper end, a distal end defining the circular opening for receiving a locking pin secured to one end of the gel sleeve, a perimeter defining the outer boundary of the circular opening formed of serged yarn for reinforcing the circular opening, a gel coating on the perimeter for preventing the overlap of sleeve material between the gel sleeve and prosthetic device, and a coating of gel on the yarns forming a portion of the knit sleeve immediately surrounding the circular opening for providing resilient flexibility to the distal end of the knit sleeve.

58 Claims, 1 Drawing Sheet

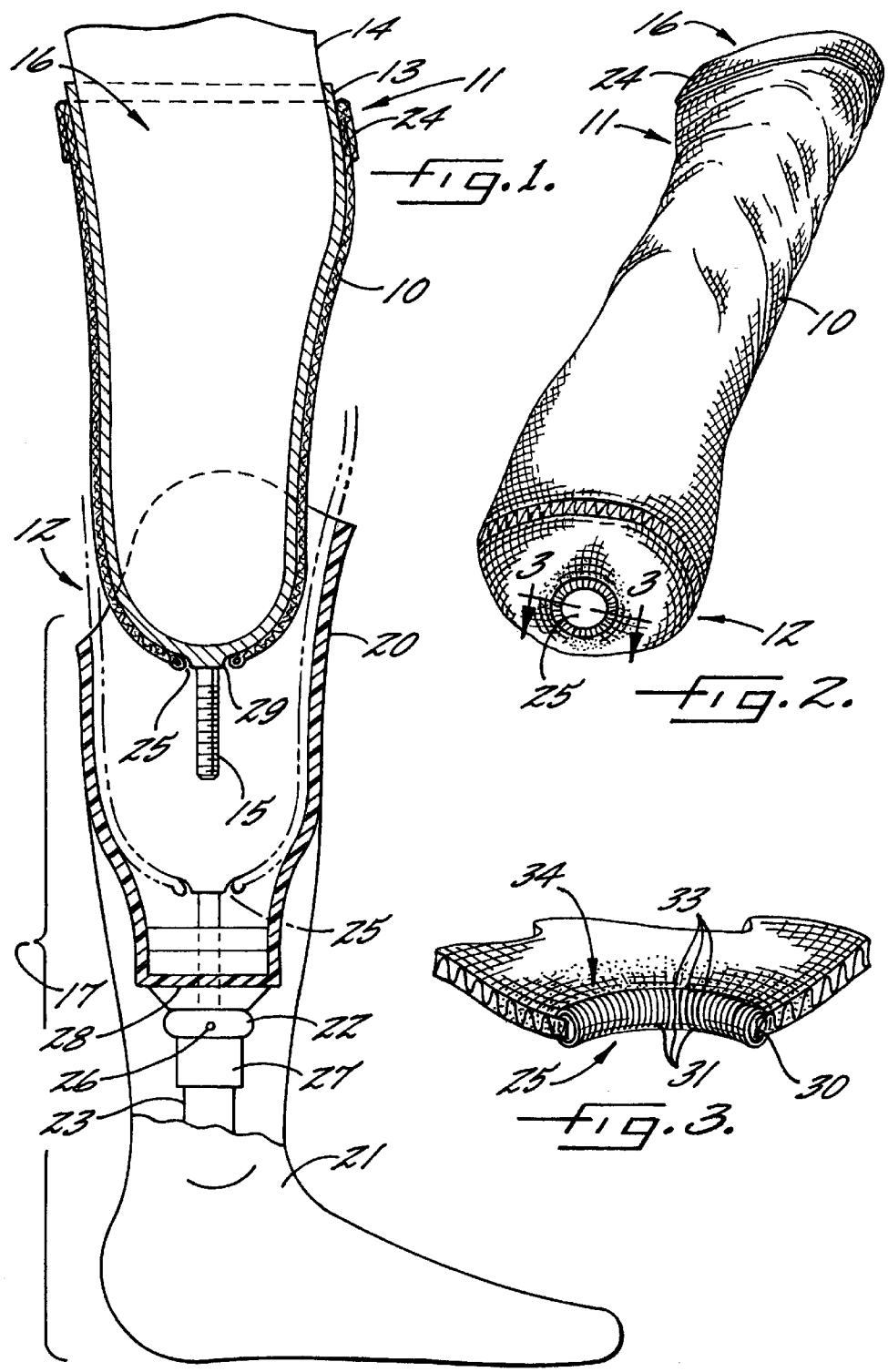

REINFORCED PROSTHETIC SLEEVE

FIELD OF THE INVENTION

The invention relates to prosthetic devices for amputees, and in particular relates to an elastic knit sleeve for use in conjunction with a conventional prosthetic device.

BACKGROUND OF THE INVENTION

Amputees who have suffered the loss of a limb, and particularly loss of a leg or portion thereof, benefit from a wide assortment of prosthetic devices. Conventional prosthetic devices provide enhanced mobility and include a variety of artificial legs that are secured to the remaining (i.e., residual) portion of a limb. In most circumstances, the length of an amputee's residual limb determines the type of prosthetic device suitable for the amputee. For example, an amputee having a residual limb extending below the knee may require a partial leg prosthesis (commonly referred to as a "transtibial"). In contrast, an amputee who has suffered the loss of at least a portion of his leg above the knee may require a full leg prosthesis (commonly referred to as a "transfemoral").

Conventional means for securing a prosthesis to a residual limb (e.g., leg) include a flexible prosthetic sleeve having a locking pin secured to the distal (i.e., lower) end thereof that is rolled on or slipped over the residual limb. It will be understood that the term locking pin refers to an elongate bolt or rod that is suitable for securing a prosthesis to a prosthetic sleeve. In general, prosthetic sleeves that include a locking pin at the distal end are typically manufactured from silicone, thus providing a flexible and durable sheath, and commonly referred to as a "gel sleeve." The gel sleeve and locking pin serve as a foundational point of attachment for a prosthesis to the residual limb.

Typical means for securing a prosthesis to a residual limb further includes a formfitting sleeve, usually knit, having an opening at the distal end that is slipped over the gel sleeve and locking pin. The knit sleeve provides a protective layer between the gel sleeve and the prosthesis. Further, the knit sleeve provides some rotational movement of the residual limb with respect to the prosthesis, thus promoting a natural gate in the amputee's stride. In other words, the knit sleeve material permits the limb covered by the gel sleeve to shift or slide when the amputee bends the limb-prosthesis combination when walking. The opening at the distal end of the knit sleeve provides a passageway through which the locking pin passes when the knit sleeve is pulled over the gel sleeve.

A conventional prosthesis further includes a form-fitting rigid fiberglass or plastic socket for supporting the residual limb. The socket is shaped to slideably receive a lower portion of the residual limb, thereby sandwiching the gel sleeve and knit sleeve between the residual limb and socket. The socket includes a cylindrical bore extending through a medial portion therethrough for receiving the locking pin when the socket is placed over the residual limb. The socket also provides a rigid framework for attaching a distal attachment device, intermediate coupling components, pylon, and a prosthetic foot.

The distal attachment device connects the socket and sleeve combination to the pylon or artificial leg by means of a conventional locking mechanism. The conventional locking mechanisms referenced herein may include threads and thread stops for engaging a corresponding pin or bolt. The locking mechanism may also include a positive lock and push button release system for locking the pin in place once it is engaged by the prosthesis. Accordingly, the locking pin extending from the distal end of the gel sleeve protrudes through the openings in the distal end of the gel sleeve and continues into the bore in the socket. Further, intermediate coupling components for securing the residual limb, covered by the gel sleeve and knit sleeve, to a prosthesis are secured therebetween by means of conventional locking mechanisms. Finally, the prosthetic foot is attached to the distal end of the prosthesis by any number of conventional locking mechanisms.

The knit sleeve has traditionally been used to provide an additional protective layer between the gel sleeve covering the residual limb and the prosthesis. An amputee may vary the number of knit sleeves depending on the size of the socket relative to the residual limb. Stated differently, an amputee may require multiple knit sleeves of varying thickness to provide a snug, secure fit between the residual limb and the socket of the prosthesis.

Conventional sockets for supporting a residual limb covered by a gel sleeve and knit sleeve and for securing an artificial leg thereto are commonly manufactured from a carbon fiber fabric and acrylic modified epoxy resin for maximum strength and minimum weight. The sockets may also be manufactured from nylon and glass fabric and polyester modified epoxy resin. As referenced above, the gel sleeves that are rolled on over the residual limb are typically made of pliable silicone. The knit sleeve provides some lateral movement of the gel sleeve relative to the socket, thereby promoting greater flexibility and increased range of motion of the artificial leg. Absent the knit sleeve, the silicone-on-epoxy resin interface between the gel sleeve and socket would result in a stiff and inflexible movement of the amputee's leg during a normal stride. The knit sleeve covering the gel sleeve also reduces frictional forces caused by the surfaces of the gel sleeve and socket in contact with one another, thus minimizing the wear on the surfaces of the prosthesis.

The normal "wear and tear" on the interior and exterior surfaces of the knit sleeve in contact with the gel sleeve and socket results in the degradation and eventual breakdown of the yarns forming the knit sleeve. This breakdown or "unraveling" of yarns comprising the sleeve is especially prevalent at the distal end portion of the knit sleeve. The distal end portion of the knit sleeve is in constant contact with the interior of the socket and, therefore, is subject to increased friction due to the rotational and lateral movement of the sleeve-covered residual limb against the interior of the socket. During the ambulatory movement of the amputee, these frictional forces result in "hot spots" at the distal end portion of the knit sleeve which tend to degrade the structure of the individual yarns forming the sleeve and eventually leads to the unraveling of the yarns. Therefore, the distal end of the knit sleeve tends to "wear out" before the remainder of the sleeve.

An elliptical slit at the distal end of typical knit sleeves for receiving a locking pin fails to provide continuous contact between the perimeter of the slit and the peripheral contour of the locking pin. The lack of continual contact around the perimeter of the elliptical slit causes the knit material forming the distal end of conventional knit sleeves to overlap and bunch during use of the prosthesis. The overlapped and bunched material contributes to increased friction, which leads to unraveling. Further, the bunching of material at the end of the knit sleeve compounds any discomfort to the amputee caused by the constant pressure of the socket against the end of the residual limb.

Further, typical methods for forming the openings at the distal end of most knit sleeves include burning or cutting the sleeve material. This technique, however, results in frayed yarn ends defining the perimeter of these conventional openings. If the perimeter lacks sufficient reinforcement, the yarns ends tend to degrade the structural integrity of the opening and thereby promote rips or "runs" that progressively extend the length of the distal end of the sleeve. The tattered knitting of the knit sleeve material accumulates between the gel sleeve and socket, thus leading to the bunching of material at the distal end of the knit sleeve.

Conventional techniques for reducing movement of a residual limb relative to a prosthesis include U.S. Pat. No. 5,728,1672 Lohman which discloses a prosthetic sock with vertical strips or patches disposed on an inner and outer surface thereof. The outer surfaces of the patches are rough to prevent the sock from slipping. Lohman includes an opening at the distal end of the sock surrounded by patches placed on the interior and exterior of the sleeve. Nevertheless, the patch surrounding the opening fails to sufficiently reinforce the yarns at the distal end of the sleeve. Thus, the yarns tend to unravel after prolonged use of the knit sleeve.

The conventional knit sleeves described above fail to address the need for a reinforced circular opening at the distal end of the sleeve for receiving the locking pin. Therefore, there is a need for a prosthetic sleeve that prevents the bunching of material at the distal end of the sleeve.

Further, there is a need for a prosthetic sleeve having reinforced yarn at the distal end to avoid discomfort and excessive wear due to the bunching.

There is an additional need for a prosthetic sleeve having a reinforced circular opening at the lower end of the sleeve to avoid the unraveling of the yarn ends forming the opening.

Accordingly, it is an object of the invention to provide a prosthetic sleeve having a defined circular opening at the distal end for receiving a locking pin affixed to an end of a gel sleeve.

It is a further object of the present invention to provide a circular opening having a reinforced perimeter for preventing the unraveling of yarns subject to the frictional forces created between the contact surfaces of the gel sleeve and socket.

It is yet a further object of the invention to provide a prosthetic sleeve having a layer of gel for coating a reinforced perimeter of the circular opening for further preventing the unraveling of the yarn.

It is yet another object to provide a prosthetic sleeve having a layer of gel covering a portion of the interior and exterior of the distal end of the sleeve immediately surrounding the circular opening for providing an additional boundary layer and for preventing the breakdown of the sleeve material at the distal end portion of the sleeve immediately surrounding the circular opening.

SUMMARY OF THE INVENTION

The invention meets these objects with an improved fabric or knit sleeve for covering a gel sleeve that includes a reinforced circular opening at the distal end of the sleeve that is sewn or serged and then optionally coated with a gel to prevent unraveling of the yarn. The sleeve is typically knit because of the beneficial elastic or "form-fitting" qualities knitting provides to articles worn on the body. Nevertheless, the present invention is not limited to a knit sleeve. The circular or round opening—as opposed to an elliptical slit-insures a conforming fit of the circular opening around the nipple or ledge at the base of the locking pin where the pin protrudes from the gel sleeve, thus reducing the likelihood of the sleeve material to bunch in areas between the gel sleeve and socket.

In practice, an amputee first pulls the gel sleeve having a locking pin attached thereto at a distal end over the residual limb, aligns the circular opening of the improved knit sleeve with the distal end of the locking pin, and then slips the knit sleeve over the gel sleeve and locking pin. Next, the amputee positions the residual limb covered by the knit sleeve and gel sleeve into the interior of the rigid socket. The socket is affixed to the residual limb by means of a conventional distal attachment device (e.g., cylindrical plate). In other words, the locking pin passes through an opening in the socket and engages a locking mechanism in an upper portion of the distal attachment device. Next, the amputee connects a lower portion of the distal attachment device to one end of a pylon with intermediate coupling components. Thereafter, the amputee secures a prosthetic foot to an opposite end of the pylon.

The reinforced circular opening at the distal end of the knit sleeve has the advantages of providing a snug fit around the periphery of the base of the locking pin (i.e., nipple) thereby minimizing the unraveling of yarns at the distal end of the sleeve and preventing accumulation of knit material between the gel sleeve and socket. Moreover, the polymer coating on the serged yarns hinders premature breakdown of the knit sleeve.

In sum, the advantages of the present invention mentioned above enhance the durability of the distal end of the knit sleeve and prevents bunching of the knit sleeve between the gel sleeve and prosthesis (i.e., socket).

The foregoing and other objects and advantages of the invention and the manner in which the same are accomplished will become clearer based on the following detailed description taken in conjunction with the accompanying drawings in which:

BRIEF DESCRIPTION OF THE DRAWINGS

FIG. 1 is a cross-sectional view of the present invention as incorporated into a prosthetic device;

FIG. 2 is a perspective view of the present invention showing a welt at an upper end of the knit sleeve and a reinforced circular opening at a distal end of the knit sleeve; and FIG. 3 is an exploded partial cross-section view taken along line 3—3 of the distal end portion of the knit sleeve.

DETAILED DESCRIPTION OF THE INVENTION

An overall view of the fabric or knit sleeve 10 for covering a gel sleeve 13 and providing enhanced durability according to the present invention is set forth in FIG. 1. As noted above, the elastic qualities of a knit sleeve are often preferred, yet, the present invention is not limited to a knit sleeve. As shown, the sleeve 10 includes an upper end 11 and distal end 12 that is slipped over the gel sleeve 13 covering a residual limb 14. The upper end 11 of the sleeve 10 is knit from cotton and spandex filament yarn sold under the trademark LYCRA®. The cotton/filament blend provides an elastic fitting material that conforms to the shape of the residual limb 14 covered by the gel sleeve 13. The upper end 11 of the sleeve 10 also includes an opening 16 for receiving a portion of the gel sleeve 13 covering the residual limb 14.

As configured, the distal end 12 of the sleeve 10 is subjected to the majority of frictional forces caused by the weight of the amputee against the prosthetic device 17 and sleeve 10 sandwiched therebetween. Accordingly, the distal end 12 of the sleeve 10 is knit from a combination of filament and spun nylon yarn.

As shown in FIG. 1, the sleeve 10 is used in conjunction with a conventional prosthetic device 17 that is removably attachable to the residual limb 14. The prosthetic device 17 includes the gel sleeve 13 for covering the residual limb 14 and for providing a point of attachment for the prosthetic device. The gel sleeve 13 is secured to prosthetic device 17 by means of a locking pin 15 secured to the distal end 12 of the gel sleeve. As referenced above, it will be understood that the term locking pin refers to a bolt or rod that is suitable for securing a prosthetic sleeve to a prosthetic device. As shown in FIG. 2, a reinforced circular opening 25 in the distal end 12 of the sleeve 10 receives the locking pin 15 when the sleeve is pulled over the gel sleeve 13.

As depicted in FIG. 1, the lower end of the locking pin 15 secures the residual limb to the prosthetic device 17. Specifically, the locking pin 15 passes through the circular opening 25 and into a cylindrical bore 28 extending through a medial portion of a socket 20 for supporting the residual limb 14. The socket 20 is formed of a rigid material (e.g., fiberglass or plastic) and shaped to conform to the general contour of the residual limb 14. The bore 28 in the socket 20 receives the locking pin 15 when the lower portion of the residual limb 14 is fitted into the socket 20. In this configuration, the sleeve 10 provides a boundary layer between the gel sleeve 13 covering the residual limb 14 and the socket 20 furnishes a base structure for supporting the weight of the amputee.

The prosthetic device 17 also includes a distal attachment device 22 having a conventional locking mechanism for securing the distal end of the locking pin 15 thereto. As configured, the distal end of the locking pin 15 passes through the bore 28 in the socket 20 and engages the distal attachment device 22.

The distal attachment device 22 is connected to one end of the pylon 23 by an intermediate coupling component 27 having conventional locking mechanisms contained therein. Accordingly, the upper portion of the intermediate coupling component 27 is releasably fastened to the lower end of the distal attachment device 22. In a preferred embodiment of the present invention as shown in FIG. 1, the intermediate coupling component 27 is secured to the distal attachment device 22 by a positive lock and release mechanism 26. In its operation, the distal attachment device 22 permits the amputee to readily attach and remove the pylon 23.

The pylon 23 extends longitudinally from the lower end of intermediate coupling component 27 and includes an artificial foot 21 secured to a lower end of the pylon. Conventional artificial feet are generally formed of a composite material, thus providing a durable and wear-resistant surface for contacting the ground during ambulatory movement of the amputee.

Referring to FIG. 1, the coaxial alignment of the locking pin 15, circular opening 25, bore 28, and locking mechanisms in the distal attachment device 22 and intermediate coupling component 27 permits the amputee to secure the prosthetic device 17 to the residual limb and walk in a relatively normal manner.

As shown in FIG. 2, the upper end 11 of the sleeve 10 includes a welt 24 formed by knitting a row of stitches across the upper end 11 of a double-folded portion of the sleeve as the sleeve is manufactured (commonly referred to as a "make-up course"). As referenced herein, it will be understood that the term course refers to the row of stitches running across a knit fabric. Accordingly, the welt 24 is an integral part of the sleeve 10. The welt 24 provides a greater resistivity to expansion at the upper end 11 of the sleeve 10 covering an upper portion of the residual limb. In general, the upper portion of an amputee's residual limb is relatively larger in diameter than the lower end of the residual limb. Consequently, the greater resistivity to expansion of the welt 24 prevents the upper end 11 of the sleeve 10 from slipping from the larger upper portion of the residual limb to the smaller lower portion of the residual limb. In other words, the welt 24 prevents the sleeve 10 from slipping down the limb and bunching between the socket 20 and gel sleeve 13.

Referring to FIG. 2, the reinforced distal end 12 of the sleeve 10 is knit from a combination of filament and spun nylon yarn and includes the circular opening 25 for receiving the locking pin 15. Any number of conventional means to include a circular die punch or heated circular die may be used to form the circular opening 25. In the case of a heated circular die, the heated edges of the die burn the circular opening 25 into the distal end 12 of the sleeve 10.

As shown in FIG. 3, an outer perimeter 30 of the circular opening is formed by serged polyester or nylon yarn 31 sewn along the outer edges of the circular opening 25. The serged yarn 31 reinforces the perimeter 30 of the circular opening 25, thereby preventing the unraveling of the yarn ends defining the perimeter. Further, the serged yarn 31 assists in maintaining the structural integrity of the circular opening 25, thus insuring a conformal or snug fit of the perimeter 30 of the opening around a nipple 29 protruding from the gel sleeve 13 around the periphery of the base portion of the locking pin 15 (see FIG. 1).

A coating of polymer 33 on the serged yarn 31 further reinforces the perimeter 30. The coating 33 also bonds the yarn ends immediately surrounding the opening 25 and prevents the yarn ends from unraveling. Moreover, the polymer coating 33 insures that the perimeter 30 of the circular opening 25 conforms to the contoured nipple 29 protruding around the base of the locking pin 15, thereby preventing the overlap of the sleeve material at the distal end 11 of the sleeve 10. In a preferred embodiment of the present invention, the polymer coating includes a gel comprised of 20–30% water, 0.5% vinyl acetate monomer, and 0.06% formaldehyde, such as that sold by Air Products Polymers, L.L.P, of Allentown, Pa., under the trade name AIRFLEX® (MSDS No. 7200).

As referenced above, the overlap of sleeve material caused by a non-circular opening promotes bunching at the distal end 11 of the sleeve 10. The bunching prevalent in conventional, non-circular openings results in increased frictional forces which, in turn, leads to the unraveling of yarn at the distal end of the sleeve 10. Further, bunching at the distal end 11 of the sleeve 10 between the gel sleeve 13 and socket 20 adds to the discomfort to the amputee.

The yarns that form a portion of the sleeve 10 immediately surrounding the circular opening 25 include a coating of polymer 34. The polymer coating 34 provides an additional reinforcement layer to the distal end 11 of the sleeve 10. The polymer coating 34 further prevents bunching and contributes to the cushioning of the distal end of the amputee's residual limb 14 against the rigid socket 20. In a preferred embodiment of the invention, the polymer coating includes a gel comprised of 20–30% water, 0.5% vinyl acetate monomer, and 0.06% formaldehyde, as described above. Advantageously, the polymer coating on the individual yarns provides more flexibility and greater resilience to the sleeve surfaces immediately surrounding the circular opening 25 as compared to conventional patches made of inelastic material.

In order to mount the prosthesis 17 to a residual limb 14, the amputee first pulls the gel sleeve 13 over the residual limb, aligns the circular opening 25 of the sleeve 10 with the locking pin 15 secured to the gel sleeve, and then pulls the sleeve over the gel sleeve 13. As the gel sleeve 13 is pulled over the residual limb 14, the locking pin 15 passes through the circular opening 25 in the sleeve 10. The distal end of the locking pin 15 passes through the bore 28 in the socket 20 when the amputee slides the sleeve-covered residual limb 14 into the interior of the socket (see FIG. 1). The socket 20 is then affixed to the residual limb 14 by the distal attachment device 22. In other words, the locking pin 15 passes through the bore 28 in the socket and is engaged by a conventional locking mechanism in the distal attachment device 22. Thereafter, the amputee secures one end of the pylon 23 having an artificial foot 21 affixed thereto by means of the intermediate coupling component 27.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A prosthetic fabric sleeve for enhancing the resistance to wear while providing improved cushioning, said fabric sleeve comprising:
    an upper end having an opening configured to receive a portion of a gel sleeve;
    a reinforced distal end for preventing yarns that form said fabric sleeve from unraveling; and
    a circular opening defined by a portion of said distal end configured to receive a locking pin that is capable of securing a prosthesis to a residual limb, said circular opening having a perimeter formed by serged yarn for reinforcing said circular opening and for preventing yarns forming said perimeter from unraveling;
    wherein said fabric sleeve is a knitted sleeve;
    wherein said perimeter comprises a polymer coating for strengthening said circular opening and for further preventing said serged yarns from unraveling.

2. A sleeve according to claim 1 wherein yarns forming a portion of said fabric sleeve immediately surrounding said circular opening include a polymer coating for preventing the accumulation of sleeve material between said gel sleeve and a socket of a prosthesis at said distal end.

3. A sleeve according to claim 1 wherein yarns forming a portion of said fabric sleeve immediately surrounding said circular opening include a coating of gel, said gel comprising water, vinyl acetate monomer, and formaldehyde to provide resilient flexibility to said portion.

4. A sleeve according to claim 1 wherein said upper end comprises a welt for resisting the expansion of said fabric sleeve at said opening, said welt comprising a double folded portion of said upper end maintained by a sewn finished edge.

5. A sleeve according to claim 1 wherein said upper end is knit of cotton and spandex yarn.

6. A sleeve according to claim 1 wherein said reinforced distal end is knit of filament and spun nylon yarn.

7. A sleeve according to claim 1 wherein said upper end is formed from material selected from the group consisting of:
    a single-ply layer of cotton and spandex yarn;
    a two-ply layer of cotton and spandex yarn; or
    a four-ply layer of cotton and spandex yarn.

8. A sleeve according to claim 1 wherein said reinforced distal end is formed from material selected from the group consisting of:
    a single-ply layer of filament and spun nylon yarn;
    a two-ply layer of filament and spun nylon yarn; or
    a four-ply layer of filament and spun nylon yarn.

9. A prosthetic fabric sleeve for enhancing the resistance to wear while providing improved cushioning, said fabric sleeve comprising:
    an upper end having an opening configured to receive a portion of a gel sleeve;
    a reinforced distal end for preventing yarns that form said fabric sleeve from unraveling; and
    a circular opening defined by a portion of said distal end positioned to receive a locking pin, said locking pin capable of securing a prosthesis to a residual limb, said circular opening having a perimeter formed by serged yarn for reinforcing said circular opening and for preventing yarns forming said perimeter from unraveling;
    wherein said fabric sleeve is a knitted sleeve and covering the residual limb;
    wherein said perimeter comprises a coating of gel, said gel comprising water, vinyl acetate monomer, and formaldehyde to provide resilient flexibility to said perimeter.

10. A sleeve according to claim 9 wherein yarns forming a portion of said fabric sleeve immediately surrounding said circular opening include a polymer coating for preventing the accumulation of sleeve material between said gel sleeve and a socket of a prosthesis at said distal end.

11. A sleeve according to claim 9 wherein yarns forming a portion of said fabric sleeve immediately surrounding said circular opening include a coating of gel, said gel comprising water, vinyl acetate monomer, and formaldehyde to provide resilient flexibility to said portion.

12. A sleeve according to claim 9 wherein said upper end comprises a welt for resisting the expansion of said sleeve at said opening, said welt comprising a double folded portion of said upper end maintained by a sewn finished edge.

13. A sleeve according to claim 9 wherein said upper end is knit of cotton and spandex yarn.

14. A sleeve according to claim 9 wherein said reinforced distal end is knit of filament and spun nylon yarn.

15. A sleeve according to claim 9 wherein said upper end is formed from material selected from the group consisting of:
    single-ply layer of cotton and spandex yarn;
    a two-ply layer of cotton and spandex yarn; or
    a four-ply layer of cotton and spandex yarn.

16. A sleeve according to claim 9 wherein said reinforced distal end is formed from material selected from the group consisting of:
    a single-ply layer of filament and spun nylon yarn;
    a two-ply layer of filament and spun nylon yarn; or
    a four-ply layer of filament and spun nylon yarn.

17. A prosthetic fabric sleeve for covering a gel sleeve for enhancing the resistance to wear while providing improved cushioning, said fabric sleeve comprising:
    an upper end having an opening configured to receive a portion of a gel sleeve;

a reinforced distal end for preventing yarns that form said fabric sleeve from unraveling; and a circular opening defined by a portion of said distal end positioned to receive a locking pin through said fabric sleeve at said opening for securing a prosthesis to a residual limb;

wherein yarns forming a portion of said fabric sleeve immediately surrounding said circular opening include a coating of gel, said gel comprising water, vinyl acetate monomer, and formaldehyde to provide resilient flexibility to said portion; wherein said fabric sleeve cover the residual limb.

18. A sleeve according to claim 17 wherein:
said fabric sleeve is a knitted sleeve; and
said circular opening has a perimeter formed by serged yarn for reinforcing said circular opening and for preventing the yarns forming from unraveling.

19. A sleeve according to claim 18 wherein said perimeter comprises a polymer coating for strengthening said sleeve at said circular opening and for further preventing said serged yarns from unraveling.

20. A sleeve according to claim 18 wherein said perimeter comprises a coating of gel, said gel comprising water, vinyl acetate monomer, and formaldehyde to provide resilient flexibility to said perimeter.

21. A sleeve according to claim 17 wherein said upper end comprises a welt for resisting the expansion of said fabric sleeve at said opening, said welt comprising a double folded portion of said upper end maintained by a sewn finished edge.

22. A sleeve according to claim 17 wherein said upper end is knit of cotton and spandex yarn.

23. A sleeve according to claim 17 wherein said reinforced distal end is knit of filament and spun nylon yarn.

24. A sleeve according to claim 17 wherein said upper end is formed from material selected from the group consisting of:
a single-ply layer of cotton and spandex yarn;
a two-ply layer of cotton and spandex yarn; or
a four-ply layer of cotton and spandex yarn.

25. A sleeve according to claim 17 wherein said reinforced distal end is formed from material selected from the group consisting of:
a single-ply layer of filament and spun nylon yarn;
a two-ply layer of filament and spun nylon yarn; or
a four-ply layer of filament and spun nylon yarn.

26. An apparatus for removably mounting a prosthesis to a residual limb comprising:
a gel sleeve configured to cover the residual limb;
a prosthetic knitted fabric sleeve covering said gel sleeve for enhancing the resistance to wear, said fabric sleeve comprising
an upper end having an opening for receiving a portion of said gel sleeve;
a reinforced distal end for preventing yarns that form said fabric sleeve from unraveling; and
a circular opening defined by a portion of said distal end, said circular opening having a perimeter formed by serged yarn for reinforcing said circular opening and for preventing yarns forming said perimeter from unraveling;
a locking pin affixed to a distal end of said gel sleeve, said locking pin capable of securing two prosthesis to two residual limb; and
an attachment means associated with said pin and said prosthesis for removably attaching said prosthesis to the residual limb;

wherein said circular opening is adapted to receive at least a portion of said locking pin.

27. An apparatus according to claim 26 wherein said attachment means comprises threads and a thread stop on said pin and corresponding threads and a stop in an interior portion of said prosthesis.

28. An apparatus according to claim 26 wherein said attachment means comprises a male member defining at least one recessed groove about its circumference and mounted on said pin and a corresponding female member in an interior portion of said prosthesis including a stud for being received in said groove for securing said male member to said prosthesis.

29. An apparatus according to claim 26 wherein said perimeter comprises a polymer coating for strengthening said sleeve at said circular opening and for further preventing said serged yarns from unraveling.

30. An apparatus according to claim 26 wherein said perimeter comprises a coating of gel, said gel comprising water, vinyl acetate monomer, and formaldehyde to provide resilient flexibility to said perimeter.

31. An apparatus according to claim 26 wherein yarns forming a portion of said fabric sleeve immediately surrounding said circular opening include a polymer coating for preventing the accumulation of sleeve material between said gel sleeve and a socket of said prosthesis at said distal end.

32. An apparatus according to claim 26 wherein yarns forming a portion of said fabric sleeve immediately surrounding said circular opening include a coating of gel, said gel comprising water, vinyl acetate monomer, and formaldehyde to provide resilient flexibility to said portion.

33. An apparatus according to claim 26 wherein said upper end comprises a welt for resisting the expansion of said fabric sleeve at said opening, said welt comprising a double folded portion of said upper end maintained by a sewn edge.

34. An apparatus according to claim 26 wherein said upper end is knit of cotton and spandex yarn.

35. An apparatus according to claim 26 wherein said reinforced distal end is knit of filament and spun nylon yarn.

36. An apparatus according to claim 26 wherein said upper end is formed from material selected from the group consisting of:
a single-ply layer of cotton and spandex yarn;
a two-ply layer of cotton and spandex yarn; or
a four-ply layer of cotton and spandex yarn.

37. An apparatus according to claim 26 wherein said reinforced distal end is formed from material selected from the group consisting of:
a single-ply layer of filament and spun nylon yarn;
a two-ply layer of filament and spun nylon yarn; or
a four-ply layer of filament and spun nylon yarn.

38. An apparatus for providing ambulatory movement to an amputee comprising:
a prosthesis for supporting a residual limb;
a gel sleeve configured to cover the residual limb, said sleeve having a locking pin affixed to a distal end of said sleeve for securing said prosthesis to said sleeve; and
a prosthetic knitted fabric sleeve covering said gel sleeve for enhancing the resistance to wear, said fabric sleeve comprising:
an upper end having an opening for receiving a portion of said gel sleeve;
a reinforced distal end for preventing yarns that form said fabric sleeve from unraveling; and a circular opening defined by a portion of said distal end for receiving at least a portion of said locking pin; said circular opening having a perimeter formed by serged yarn for reinforcing said circular opening and for preventing yarns forming said perimeter from unraveling.

39. An apparatus according to claim 38 wherein said prosthesis comprises:
a prosthetic socket for slideably receiving a residual limb covered by said gel sleeve and said fabric sleeve, said socket having a cylindrical bore extending through a medial portion of said socket for receiving said locking pin;
an attachment device for attaching said gel sleeve to said prosthetic socket;
a pylon for supporting said prosthetic socket having an artificial foot attached at a distal end thereto for contacting the ground; and
an intermediate coupling component for coupling said attachment device to said pylon.

40. An apparatus according to claim 38 wherein said perimeter comprises a polymer coating for strengthening said circular opening and for further preventing said serged yarn forming said perimeter from unraveling.

41. An apparatus according to claim 38 wherein said perimeter comprises a coating of gel, said gel comprising water, vinyl acetate monomer, and formaldehyde to provide resilient flexibility to said perimeter.

42. An apparatus according to claim 38 wherein yarns forming a portion of said fabric sleeve immediately surrounding said circular opening include a polymer coating for preventing the accumulation of sleeve material between said gel sleeve and said prosthesis at said distal end.

43. An apparatus according to claim 38 wherein yarns forming a portion of said fabric sleeve immediately surrounding said circular opening include a coating of gel, said gel comprising water, vinyl acetate monomer, and formaldehyde to provide resilient flexibility to said portion.

44. An apparatus according to claim 38 wherein said upper end comprises a welt for resisting the expansion of said fabric sleeve at said opening, said welt comprising a double folded portion of said upper end maintained by a sewn finished edge.

45. An apparatus according to claim 38 where in said upper end is knit of cotton and spandex yarn.

46. An apparatus according to claim 38 wherein said reinforced distal end is knit of filament and spun nylon yarn.

47. An apparatus according to claim 38 wherein said upper end is formed from material selected from the group consisting of:
a single-ply layer of cotton and spandex yarn; or
a multi-ply layer of cotton and spandex yarn.

48. An apparatus according to claim 38 wherein said reinforced distal end is formed from material selected from the group consisting of:
a single-ply layer of filament and spun nylon yarn; or
a multi-ply layer of filament and spun nylon yarn.

49. An apparatus for providing ambulatory movement to an amputee comprising:
a prosthesis for supporting a residual limb;
a gel sleeve configured to cover the residual limb, said sleeve having a locking pin affixed to a distal end of said sleeve for securing said prosthesis to said sleeve; and
a prosthetic knitted fabric sleeve covering said gel sleeve for enhancing the resistance to wear, said fabric sleeve comprising:
an upper end having an opening for receiving a portion of said gel sleeve;
a reinforced distal end for preventing yarns that form said fabric sleeve from unraveling; and
a circular opening defined by a portion of said distal end for receiving at least a portion of said locking pin;
wherein yarns forming a portion of said fabric sleeve immediately surrounding said circular opening include a coating of gel, said gel comprising water, vinyl acetate monomer, and formaldehyde to provide resilient flexibility to said portion.

50. An apparatus according to claim 49 wherein said prosthesis comprises:
a prosthetic socket for slideably receiving a residual limb covered by said gel sleeve and said fabric sleeve, said socket having a cylindrical bore extending through a medial portion of said socket for receiving said locking pin;
an attachment device for attaching said gel sleeve to said prosthetic socket;
a pylon for supporting said prosthetic socket having an artificial foot attached at a distal end thereto for contacting the ground; and
an intermediate coupling component for coupling said attachment device to said pylon.

51. An apparatus according to claim 49 wherein:
said fabric sleeve is a knitted sleeve; and
said circular opening has a perimeter formed by serged yarn for reinforcing said circular opening and for preventing the yarns forming said perimeter from unraveling.

52. An apparatus according to claim 51 wherein said perimeter comprises a polymer coating for strengthening said circular opening and for further preventing said serged yarn forming said perimeter from unraveling.

53. An apparatus according to claim 51 wherein said perimeter comprises a coating of gel, said gel comprising water, vinyl acetate monomer, and formaldehyde to provide resilient flexibility to said perimeter.

54. An apparatus according to claim 49 wherein said upper end comprises a welt for resisting the expansion of said fabric sleeve at said opening, said welt comprising a double folded portion of said upper end maintained by a sewn finished edge.

55. An apparatus according to claim 49 wherein said upper end is knit of cotton and spandex yarn.

56. An apparatus according to claim 49 wherein said reinforced distal end is knit of filament and spun nylon yarn.

57. An apparatus according to claim 49 wherein said upper end is formed from material selected from the group consisting of:
a single-ply layer of cotton and spandex yarn; or
a multi-ply layer of cotton and spandex yarn.

58. An apparatus according to claim 49 wherein said reinforced distal end is formed from material selected from the group consisting of:
a single-ply layer of filament and spun nylon yarn; or
a multi-ply layer of filament and spun nylon yarn.

* * * * *

UNITED STATES PATENT AND TRADEMARK OFFICE
CERTIFICATE OF CORRECTION

PATENT NO. : 6,440,172 B1
APPLICATION NO. : 09/397311
DATED : August 27, 2002
INVENTOR(S) : Davant, Jr. et al.

It is certified that error appears in the above-identified patent and that said Letters Patent is hereby corrected as shown below:

In Column 7, line 42, the words --and covering the residual limb-- should be after the words "knitted sleeve".

In Column 8, line 63, the words "for covering a gel sleeve" should be deleted.

In Column 9, line 63, the words "two" should be corrected to read --the--.

Signed and Sealed this

Eleventh Day of March, 2008

JON W. DUDAS
*Director of the United States Patent and Trademark Office*